United States Patent
Fan et al.

(10) Patent No.: US 11,951,228 B2
(45) Date of Patent: Apr. 9, 2024

(54) HEMOSTATIC COMPOSITION AND PREPARATION METHOD THEREFOR

(71) Applicant: Zhejiang University, Hangzhou (CN)

(72) Inventors: Jie Fan, Hangzhou (CN); Lisha Yu, Hangzhou (CN); Liping Xiao, Hangzhou (CN); Hao Chen, Hangzhou (CN); Xiaoqiang Shang, Hangzhou (CN)

(73) Assignee: Zhejiang University, Hangzhou (CN)

( * ) Notice: Subject to any disclaimer, the term of this patent is extended or adjusted under 35 U.S.C. 154(b) by 267 days.

(21) Appl. No.: 17/298,945

(22) PCT Filed: Jan. 28, 2020

(86) PCT No.: PCT/CN2020/074061
§ 371 (c)(1),
(2) Date: Jun. 1, 2021

(87) PCT Pub. No.: WO2020/108670
PCT Pub. Date: Jun. 4, 2020

(65) Prior Publication Data
US 2022/0062496 A1    Mar. 3, 2022

(30) Foreign Application Priority Data
Dec. 1, 2018   (CN) .......................... 201811461203.5

(51) Int. Cl.
*A61L 24/10* (2006.01)
*A61L 24/00* (2006.01)
*A61L 24/08* (2006.01)

(52) U.S. Cl.
CPC ......... *A61L 24/108* (2013.01); *A61L 24/0015* (2013.01); *A61L 24/0036* (2013.01); *A61L 24/0068* (2013.01); *A61L 24/08* (2013.01)

(58) Field of Classification Search
CPC .............. A61L 24/108; A61L 24/0015; A61L 24/0036; A61L 24/0068; A61L 24/08
See application file for complete search history.

(56) References Cited

FOREIGN PATENT DOCUMENTS

| CN | 101104080 | * | 4/2007 |
| CN | 102049239 | A | 5/2011 |
| CN | 107233614 | A | 10/2017 |
| CN | 108159476 | A | 6/2018 |
| WO | 2008076407 | A | 6/2008 |
| WO | 2009155600 | A | 12/2009 |
| WO | 2014145255 | A | 9/2014 |

OTHER PUBLICATIONS

Li et al. (acta Pharmacologica Sinica (2013) 34:367-372).*
Shah et al. (Adv. Ther (2018) 35:31-42).*
Meng Hui, Mao Junqin, Liu changsheng, Wei Jie. Application of mesoporous molecular sieves in medicine. Journal of Pharmaceutical Practice.
Juliana Bergamasco Laurenti a, Gabriel Zazeri a, Ana Paula Ribeiro Povinelli, et al. Enhanced pro-coagulant hemostatic agents based on nanometric zeolites. Microporous and Mesoporous Materials.

* cited by examiner

*Primary Examiner* — Shirley V Gembeh

(57) ABSTRACT

Provided is a hemostatic composition comprising trypsin and zeolite, wherein pore channels of the zeolite are micropores, the zeolite contains divalent metal cations, and the mass ratio of the trypsin to the zeolite is 1:200-4:10. In the present invention, the trypsin specifically binds to the zeolite, allowing the trypsin to maintain a certain conformation on the surface of the zeolite and to obtain a higher procoagulant activity, thereby obtaining a hemostatic composition with an excellent blood coagulation effect. The hemostatic composition of the present invention has the advantages of a simple preparation method, low cost and convenient use, and can be widely used in hemostasis during trauma and operations, especially in emergent hemostasis in hemophilia patients.

11 Claims, 3 Drawing Sheets

US 11,951,228 B2

HEMOSTATIC COMPOSITION AND PREPARATION METHOD THEREFOR

CROSS REFERENCE TO RELATED APPLICATIONS

This application is a national stage application of International application number PCT/CN2020/074061, filed Jan. 28, 2020, titled "Hemostatic Composition And Preparation Method Therefor," which claims the priority benefit of Chinese Patent Application No. 201811461203.5, filed on Dec. 1, 2018, which is hereby incorporated by reference in its entirety.

TECHNICAL FIELD

The disclosure belongs to the technical field of biomedical materials, and specifically relates to a hemostatic composition and a preparation method thereof.

BACKGROUND OF THE DISCLOSURE

Humans (including animals) can be injured in a variety of situations. In some cases, the trauma and bleeding are minor, and in addition to the application of simple first aid, only regular coagulation is required to stop bleeding normally. However, unfortunately, massive bleeding may occur in many accidental situations. For example, skin cuts or penetrating injuries (caused by knife cuts or bullets) can result in aortic damage. Most of the blood of will be lost and a normal person will die within a few minutes. Therefore, in the emergency treatment of sudden accidents in daily life, the trauma hemostasis during the operation of the patients, especially the rescue of the wounded soldiers in the war, effective and rapid hemostasis for the patients is very important.

Currently, many hemostatic materials have been developed, such as dehydrated zeolite/binder (U.S. Pat. No. 4,822,349), partially hydrated zeolite (U.S. Pat. No. 7,858,123), kaolin/gauze composite (U.S. Pat. No. 7,604,819) and a combination of zeolite and kaolin (U.S. Pat. No. 8,703,634). Whether it is a natural function of blood coagulation or the use of hemostatic materials to promote blood coagulation, the coagulation process must strictly follow each step of clotting cascade to achieve the purpose of blood coagulation, and each step of clotting cascade requires a certain time, as shown in FIG. 1. Each step of reaction process refers to the formation of an activate coagulation factor from a coagulation factor. For example, in FIG. 1, XIIa (the activated coagulation factor of XII) is formed from the coagulation factor XII, and IXa is formed from the coagulation factor IX. If one of the reactions is obstructed, the clotting cascade will fail to function normally and blood coagulation cannot be achieved. At present, the inorganic hemostatic material represented by zeolite, the process of promoting blood coagulation must follow the intrinsic pathway, that is, the following reaction process must be strictly followed: first, zeolite activates coagulation factor XII to form XIIa, thereby triggering the intrinsic pathway; then XIIa activates coagulation factor XI to form XIa, then XIa activates coagulation factor IX to form IXa, and then IXa activates coagulation factor X to form Xa; coagulation factor Xa activates coagulation factor II to form thrombin, and then thrombin cuts fibrinogen to form fibrin monomers, and finally forms cross-linked fibrin clot under the action of coagulation factor XIIIa. The multi-step reaction from zeolite activation of coagulation factor XII to the final formation of cross-linked fibrin takes 2 to 6 minutes in total. Although zeolite can promote the coagulation process, long coagulation time will result in excessive hemorrhage, and some important organs will be irreversibly damaged.

In addition, patients with hemophilia are congenital lack of coagulation factors VIII, IX, and XI in the clotting cascade and cannot achieve blood coagulation. For patients with hemophilia, hemostasis is far more difficult than normal person. It is necessary to add biological hemostatic agents to achieve blood coagulation. Commercial biological hemostatic agents include thrombin, fibrin glue, etc. As shown in FIG. 1, the coagulation function of thrombin is that thrombin directly cuts fibrinogen to form fibrin monomers, and finally forms cross-linked fibrin clot under the action of coagulation factor XIIIa. The general clotting time is 0.5-1 min. Fibrin glue can provide thrombin and fibrinogen, so it can realize the blood coagulation. Generally, the coagulation time is 0.5-1 min. Among them, thrombin is used to cut fibrinogen and at the same time promote the formation of factor XIIIa; the fibrin monomers are cross-linked with each other under the action of XIIIa to form a stable cross-linked fibrin clot, thereby preventing blood loss. However, the manufacture of thrombin or fibrin glue is difficult, the purity requirements are high, the storage conditions (−20° C.) are harsh, and the cost is very high (the market price of thrombin is generally 2000 yuan/mg; the market price of fibrin glue is generally 8000 yuan/package, one-time usage), which leads to its low practical and commercial value.

Zeolite is a commonly used inorganic material. Enzyme is a biological material that accelerates biological reactions. The combination of inorganic and biological materials presents a great challenge. The main reason is that zeolite is a "rigid" inorganic material, and enzymes are "flexible" biological macromolecules. When the enzyme is in contact with the surface of zeolite, the rigid zeolite surface easily changes the "flexible" properties of the enzyme, leading to the conformation changes of enzyme; and a part of the enzyme contacts with the surface of zeolite, which reduces the possibility of combination with the reactant. The reaction rate will be decreased, and the activity of enzyme will be reduced. Therefore, the introduction of enzymes on the surface of zeolite will cause different degrees of inactivation of the enzyme. For example, zeolite is an inorganic hemostatic material, and thrombin is a highly effective biological hemostatic agent; but when the two materials are combined, most of the thrombin (94%) is inactivated on the surface of the zeolite, and the clotting time of thrombin is extended from 0.5 min to 2.2 min (FIG. 4), and the effect of hemostasis is far from the requirements of emergency hemostasis. At present, the prior art has not yet achieved any bio-inorganic hemostatic material that is efficient, inexpensive and effective for hemophilia.

SUMMARY OF THE DISCLOSURE

In view of the shortcomings of the prior art, the technical problem to be solved by the present disclosure is to provide a bio-inorganic hemostatic composition that is fast in achieving hemostasis, low in cost, and effective for hemophilia. In the instant study, the inventors controlled the interaction between the zeolite and the enzyme and the conformation of enzyme on the surface of the zeolite by experimenting with and selecting a specific type of zeolite, an enzyme with a specific performance, and a specific mass ratio of zeolite to the enzyme, and modifying the surface of the zeolite. A bio-inorganic hemostatic material that is efficient, inexpensive and effective for hemophilia has been unexpectedly prepared for the first time, which breaks the conventional thought process and common expectation. The inventors controlled the pore size and the divalent metal cations of the zeolite, the mass ratio of trypsin to zeolite according to the mass ratio of 1:200 to 4:10, and the combinatorial effect of the above methods to standardize and stabilize the conformation of enzyme on the surface of zeolite. The inventors unexpectedly discovered that trypsin does not enter the internal framework of zeolite, and trypsin is arranged on the surface of zeolite according to the regular conformation and orientation (FIG. 2). In particular, the active site of trypsin does not face the surface of zeolite, which is beneficial to capture the reactant. By designing this special hemostatic composition, the highly efficient combination of inorganic and biological materials was unexpectedly realized, and the technical problem of enzyme inactivation on the surface of zeolite was overcome. The activity of trypsin in the hemostatic composition of the present disclosure not only does not decrease, but the hemostatic effect of the hemostatic composition is greatly improved compared with trypsin and zeolite, and the clotting time is greatly reduced (FIG. 3). The hemostatic composition of the present disclosure does not involve expensive biological agents such as thrombin, and only requires cheap and easily available trypsin to be specifically combined with a zeolite with micropores and divalent cations in a specific ratio. The purpose of fast coagulation, low cost, and effective hemostasis for hemophilia is achieved.

The present disclosure adopts the following technical solutions: the present disclosure uses a simple method to obtain a novel hemostatic composition, and the hemostatic composition at least includes zeolite and trypsin, wherein the pores of the zeolite are micropores, the zeolite contains divalent metal cations, and the mass ratio of the trypsin to the zeolite is 1:200-4:10 (FIG. 2).

Further, the divalent metal cations described in the present invention belong to the metal cations outside the zeolite framework; the metal cations outside the zeolite framework are cations that balance the negative charge of the zeolite framework and are located in the channels and cages of the zeolite.

The micropores of zeolite in the present disclosure have a pore diameter of less than 2 nm.

In some embodiments, the divalent metal cations are selected from the group consisting of cobalt ion, nickel ion, calcium ion, magnesium ion and strontium ion.

In some embodiments, the mass ratio of the trypsin to the zeolite is 1:100 to 3:10; preferably, the mass of the trypsin to the zeolite is 1:60 to 2.5:10; preferably, the mass ratio of trypsin to zeolite is 1:50 to 2:10; preferably, the mass ratio of trypsin to zeolite is 1:40 to 1.5:10; preferably, the mass ratio of trypsin to zeolite is 1:20 to 1:10.

In some embodiments, the number of divalent metal cations accounts for 50% to 95% of the total number of the metal cations outside the zeolite framework; preferably, the number of divalent metal cations accounts for 60% to 90% of the total number of the metal cations outside the zeolite framework; preferably, the number of divalent metal cations accounts for 65% to 85% of the total number of the metal cations outside the zeolite framework; preferably, the number of divalent metal cations accounts for 70% to 80% of the total number of the metal cations outside the zeolite framework; preferably, the number of divalent metal cations accounts for 72% to 78% of the total number of the metal cations outside the zeolite framework.

In some embodiments, the atomic ratio of silicon to aluminum of the zeolite is 1-20; preferably, the atomic ratio of silicon to aluminum of the zeolite is 1.2-15; preferably, the atomic ratio of silicon to aluminum of the zeolite is 1.5-4; preferably, the atomic ratio of silicon to aluminum of the zeolite is 2-3.

In some embodiments, the zeolite is selected from the group consisting of zeolite A, chabazite, zeolite β, mordenite, zeolite X, zeolite Y, and zeolite ZSM-5.

The second object of the present disclosure is to provide a method for preparing a hemostatic composition, which includes the following steps:
  (1) prepare a suspension of zeolite, wherein the pores of the zeolite are micropores and the zeolite contains divalent metal cations;
  (2) mix the suspension of zeolite and trypsin;
  (3) the trypsin is adsorbed on the surface of the zeolite to obtain the hemostatic composition.

In some embodiments, the mass ratio of zeolite to deionized water in the suspension of zeolite is 1:0.5 to 1:20; preferably, the mass ratio of zeolite to deionized water in the suspension of zeolite is 1:0.8 to 1:10; preferably, preferably, the mass ratio of zeolite to deionized water in the suspension of zeolite is 1:1 to 1:5; preferably, preferably, the mass ratio of zeolite to deionized water in the suspension of zeolite is 1:1.5 to 1:2.5.

In some embodiments, the suspension of the zeolite in the step (1) is subjected to ultrasonic treatment.

In some embodiments, the time of the ultrasonic treatment is 0.5-30 min, the ultrasonic frequency is 20-200 kHz, and the ultrasonic power is 200-5000 W.

In some embodiments, the temperature of the mixing treatment in the step (2) is 10 to 37° C.; preferably, the temperature of the mixing treatment in the step (2) is 15 to 30° C.; preferably, the temperature of the mixing treatment in the step (2) is 20 to 25° C.

In some embodiments, the step (3), after the trypsin is adsorbed on the surface of the zeolite, further includes freeze-drying the suspension of the zeolite and the trypsin. Preferably, the temperature of the freeze-drying process is 0° C. to −80° C.; preferably, the temperature of the freeze-drying process is −10° C. to −60° C.; preferably, the temperature of the freeze-drying process is −20° C. to −50° C.; preferably, the temperature of the freeze-drying process is −30° C. to −45° C.

In some embodiments, the mass ratio of trypsin to zeolite is 1:200 to 4:10; preferably, the mass ratio of trypsin to zeolite is 1:100 to 3:10; preferably, the mass ratio of trypsin to zeolite is 1:60 to 2.5:10; preferably, the mass ratio of the trypsin to zeolite is 1:50 to 2:10; preferably, the mass ratio of the trypsin to zeolite is 1:40 to 1.5:10; preferably, the mass ratio of the trypsin to zeolite is 1:20 to 1:10.

The third object of the present disclosure is to provide a hemostatic composite material, and the hemostatic composite material comprising any one of the forms of hemostatic composition as described above and an additive.

In some embodiments, the additive is selected from the group consisting of carriers, antibacterial materials, antistatic materials, and polymer polysaccharides.

In some embodiments, the carriers are the matrixes for contacting the hemostatic composition with the wound.

In some embodiments, the antibacterial materials are the agents with the function of killing or inhibiting microorganisms.

In some embodiments, the carriers are selected from the group consisting of cotton, silk, wool, plastic, cellulose, rayon, polyester, polyurethane, polyethylene foam, polyacrylic acid foam, low-density polyether, polyvinyl alcohol, and polymethyl methacrylate.

In some embodiments, the antibacterial materials are selected from the group consisting of silver nanoparticles, vanillin, and ethyl vanillin compounds.

In some embodiments, the polymer polysaccharides are selected from the group consisting of cellulose, lignin, starch, chitosan, and agarose.

The fourth object of the present disclosure is to provide the applications of any form of hemostatic composition as described above or any form of hemostatic composite material as described above in the field of hemostasis.

The beneficial effects of the present disclosure are:

1. The coagulation effect of the hemostatic composition is far better than that of zeolite or trypsin alone, and the coagulation time is greatly shortened. In the event of sudden and unexpected bleeding, the hemostatic composition can stop bleeding efficiently, lower the risk of death from aortic bleeding, and reduce the damage of vital organs. At the same time, the hemostatic composition can also stop bleeding in a very short time for hemophilia patients.

2. At present, for the emergency situation of aortic bleeding and the special situation of bleeding in hemophilia patients, the most effective hemostatic material is blood products represented by thrombin. But blood products are expensive (the price of thrombin is 2,000 yuan/mg), the content of blood component is scarce (blood products need to be extracted from human or animal blood), and storage is very difficult (blood products need to be stored at low temperature, and it inevitably loses activity outside the body). Trypsin (0.1 yuan/mg) and zeolite ($3\times10^{-7}$ yuan/mg) are both inexpensive. Through the specific binding of inorganic materials and biological macromolecules, the hemostatic composition can promote blood coagulation. The performance is equal to or even better than that of thrombin, can greatly reduce the cost of hemostatic materials, and has more commercial prospects. Especially for patients with hemophilia, the hemostatic composition can be used as a portable hemostatic material to reduce the risk of bleeding and reduce the cost of hemostatic drugs.

DETAILED DESCRIPTION OF THE PREFERRED EMBODIMENT

Figure 1:
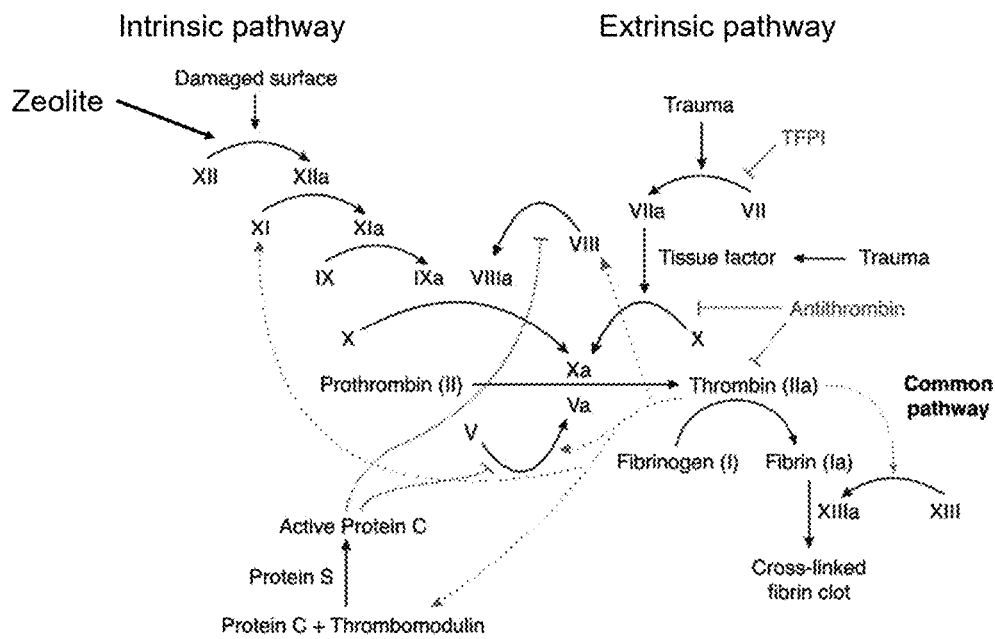
FIG. 1 is a schematic diagram of the clotting cascade.
Figure 2:
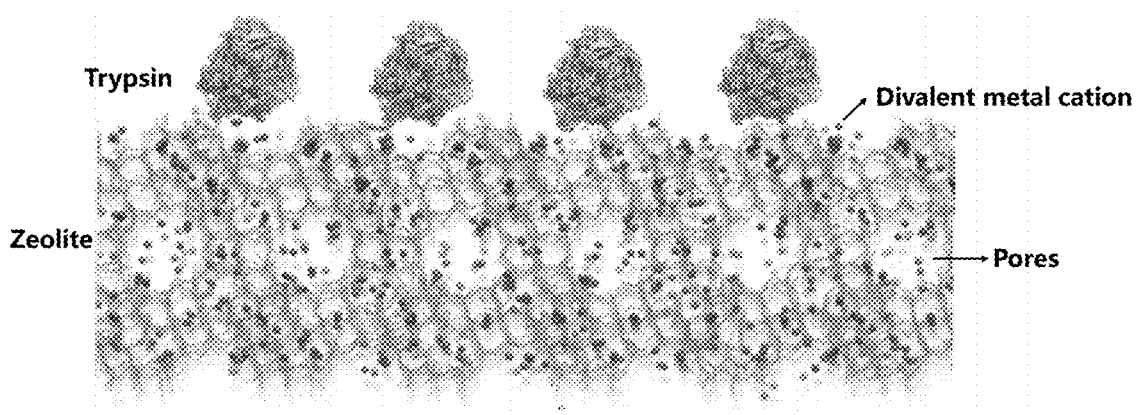
FIG. 2 is a schematic diagram of the structure of the hemostatic composition of the present disclosure.

The present disclosure is further described below with reference to the drawings and embodiments.

Evaluation of Coagulation Effect (1) Clotting Time of Natural Coagulation

Take 25 mg of the sample into a 2 mL centrifuge tube, perform an in vitro coagulation experiment at 37° C., and heat the normal blood at 37° C. for half an hour. Then, add 20 µL of 0.2M $CaCl_2$, and finally add 1 mL of normal blood. The clotting time is recorded when the normal blood turns into blood clot.

(2) Clotting Time of Coagulation Factor X Deficient Blood

Take 25 mg of the sample into a 2 mL centrifuge tube, perform an in vitro coagulation experiment at 37° C., and heat the coagulation factor X deficient blood at 37° C. for half an hour. Then, add 20 µL of 0.2M $CaCl_2$, and finally add 1 mL of coagulation factor X deficient blood. The clotting time is recorded when the coagulation factor X deficient blood turns into blood clot.

(3) Clotting Time of Coagulation Factor VIII Deficient Blood

Take 25 mg of the sample into a 2 mL centrifuge tube, perform an in vitro coagulation experiment at 37° C., and heat the coagulation factor VIII deficient blood at 37° C. for half an hour. Then, add 20 µL of 0.2M $CaCl_2$, and finally add 1 mL of coagulation factor VIII deficient blood. The clotting time is recorded when the coagulation factor VIII deficient blood turns into blood clot.

(4) Clotting Time of Coagulation Factor IX Deficient Blood

Take 25 mg of the sample into a 2 mL centrifuge tube, perform an in vitro coagulation experiment at 37° C., and heat the coagulation factor IX deficient blood at 37° C. for half an hour. Then, add 20 µL of 0.2M $CaCl_2$, and finally add 1 mL of coagulation factor IX deficient blood. The clotting time is recorded when the coagulation factor IX deficient blood turns into blood clot.

(5) Clotting Time of Coagulation Factor XI Deficient Blood

Take 25 mg of the sample into a 2 mL centrifuge tube, perform an in vitro coagulation experiment at 37° C., and heat the coagulation factor XI deficient blood at 37° C. for half an hour. Then, add 20 µL of 0.2M $CaCl_2$, and finally add 1 mL of coagulation factor XI deficient blood. The clotting time is recorded when the coagulation factor XI deficient blood turns into blood clot.

Comparative Example 1

The natural coagulation time is defined as the time required from flowing fluid to blood clot.

Evaluation of natural coagulation time: in vitro coagulation experiment was carried out at 37° C., and normal blood was kept at 37° C. in a water bath for half an hour. Then, 20 µL of 0.2M $CaCl_2$ solution was added to a 2 mL centrifuge tube, and 1 mL of normal blood was added. The clotting time of normal blood was recorded as the natural coagulation time (9.6 min).

Comparative Example 2

Evaluation of the Coagulation Effect of Zeolite A:

(1) Zeolite A (Na type, the number of monovalent sodium ions accounts for 100% of the total number of the metal cations outside the zeolite framework) with the atomic ratio of silicon to aluminum of 2 is impregnated with a 5 M magnesium chloride solution at room temperature for 12 h to obtain the zeolite A. The Zeolite A contains divalent magnesium ions and the number of divalent magnesium ions accounts for 95% of the total number of the metal cations outside the zeolite framework, and the number of monovalent sodium ions accounts for 5%.

(2) Take 25 mg of the sample into a 2 mL centrifuge tube, perform an in vitro coagulation experiment at 37° C., and heat the normal blood at 37° C. for half an hour. Then, add 20 µL of 0.2 M $CaCl_2$, and finally add 1 mL of normal blood. The clotting time is recorded as the coagulation time of zeolite A (2.8 min) as shown in Table 1, which shows that coagulation effect of zeolite A is ordinary.

Take 25 mg of zeolite A and add it to a 2 mL centrifuge tube, perform an in vitro coagulation experiment at 37° C., and heat the coagulation factor X, VIII, IX and XI deficient blood at 37° C. for half an hour. Then add 20 μL 0.2 M $CaCl_2$, and finally add 1 mL coagulation factor X, VIII, IX and XI deficient blood. The clotting time is recorded as the coagulation time of zeolite A. However, all above-mentioned deficient blood did not coagulate for a long time (Table 1), which shows that zeolite A has no procoagulant effect on patients with hemophilia.

Comparative Example 3

Evaluation of the Coagulation Effect of Trypsin:
(1) Take 25 mg of the trypsin into a 2 mL centrifuge tube, perform an in vitro coagulation experiment at 37° C., and heat the normal blood at 37° C. for half an hour. Then, add 20 μL of 0.2 M $CaCl_2$, and finally add 1 mL of normal blood. The clotting time is recorded as the coagulation time of trypsin (4 min), which shows that coagulation effect of trypsin is ordinary.
(2) Take 25 mg of trypsin and add it to a 2 mL centrifuge tube, perform an in vitro coagulation experiment at 37° C., and heat the coagulation factor X, VIII, IX and XI deficient blood at 37° C. for half an hour. Then add 20 μL 0.2M $CaCl_2$, and finally add 1 mL coagulation factor X, VIII, IX and XI deficient blood. The clotting time of coagulation factor X, VIII, IX and XI deficient blood was 4, 4.6, 4 and 4 min, respectively, which shows that coagulation effect of trypsin is ordinary.

Comparative Example 4

Figure 3:
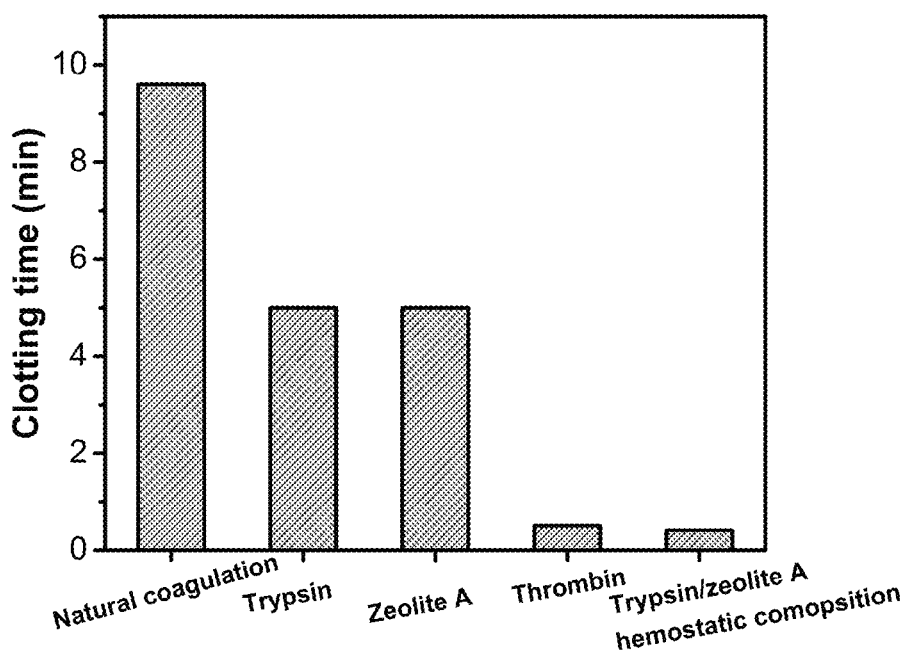
FIG. 3 is a comparison diagram of the coagulation effect of natural coagulation, trypsin, zeolite A, thrombin and trypsin/zeolite A hemostatic composition of the present disclosure.

Evaluation of the Coagulation Effect of Thrombin:
(1) Take thrombin (Sigma T4648 thrombin, Sigma-Aldrich) to make a 1 mg/mL solution, add 50 μL to a 2 mL centrifuge tube, perform in vitro coagulation experiments at 37° C. And normal blood was kept at 37° C. in a water bath for half an hour. Then, add 20 μL of 0.2 M $CaCl_2$, and finally add 1 mL of normal blood. The clotting time of normal blood was recorded as the coagulation time of thrombin (0.5 min), which has a great procoagulant effect (FIG. 3).
(2) Take thrombin (Sigma T4648 thrombin, Sigma-Aldrich) to make a 1 mg/mL solution, add 50 μL to a 2 mL centrifuge tube, perform in vitro coagulation experiments at 37° C. And coagulation factor X, VIII, IX and XI deficient blood were kept at 37° C. in a water bath for half an hour. Then add 20 μL 0.2M $CaCl_2$, and finally add 1 mL coagulation factor X, VIII, IX and XI deficient blood. The clotting time of coagulation factor X, VIII, IX and XI deficient blood was 0.5, 0.52, 0.51, 0.54 min, respectively, which shows that coagulation effect of thrombin is great (Table 1).

Comparative Example 5

Preparation of thrombin/zeolite composite: disperse 5 g of zeolite A in 30 mL of distilled water; dissolve thrombin in a phosphate buffer with a pH of 7.0 to obtain 10 mL of thrombin solution with a mass concentration of 0.1% (Sigma T4648 thrombin, Sigma-Aldrich); then the two were mixed in a volume ratio of 3:1 to prepare 40 mL of a mixed solution of zeolite A and thrombin in a weight ratio of 10:1. Under stirring conditions, add 0.5 g of glycerol and 1 g of mannitol, and add 50 μL calcium chloride solution (mass concentration of 5%) drop by drop, mix well, and then add 250 μL of glutaric acid with volume concentration of 1% dropwise under stirring. The aldehyde solution was cross-linked, then poured into a mold of appropriate shape, and placed for 2 h. After the gel was formed, freeze at −20° C. for 24 h, then freeze-thy at −40° C. for 36 h. The thrombin/zeolite composite is obtained after pouring the mold, grinding, and encapsulating.

Figure 4:
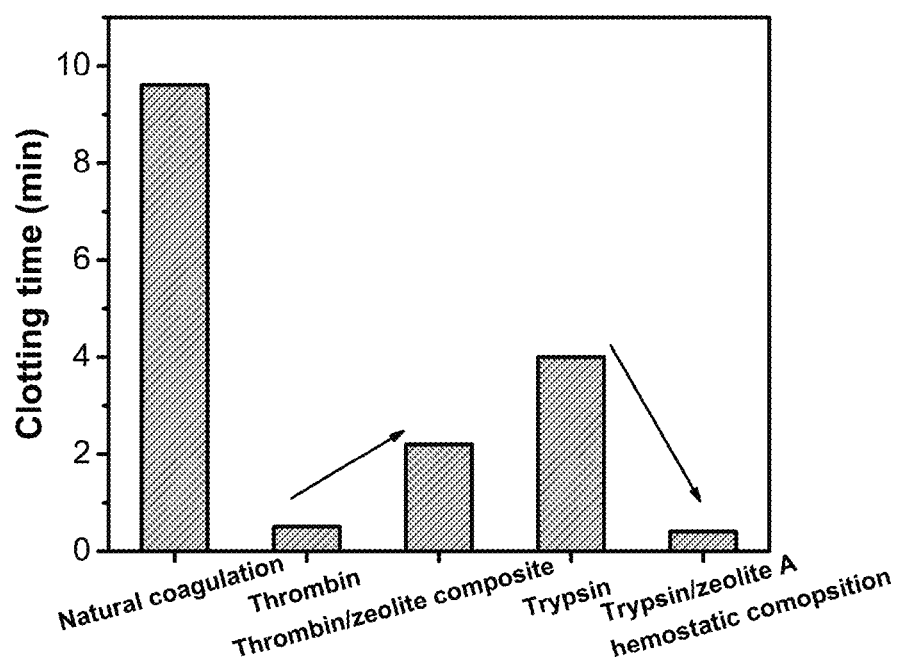
FIG. 4 is a comparison diagram of the coagulation effect of natural coagulation, thrombin, thrombin/zeolite composite, trypsin, and trypsin/zeolite A hemostatic composition of the present disclosure.

Evaluation of the Coagulation Effect of Thrombin/Zeolite Composite:
(1) Take 25 mg of the thrombin/zeolite composite into a 2 mL centrifuge tube, perform an in vitro coagulation experiment at 37° C., and heat the normal blood at 37° C. for half an hour. Then, add 20 μL of 0.2 M $CaCl_2$, and finally add 1 mL of normal blood. The clotting time is recorded as the coagulation time of thrombin/zeolite composite (2.2 min). The coagulation effect of thrombin in the thrombin/zeolite composite is decreased.
(2) Take 25 mg of thrombin/zeolite composite and add it to a 2 mL centrifuge tube, perform an in vitro coagulation experiment at 37° C., and heat the coagulation factor X, VIII, IX and XI deficient blood at 37° C. for half an hour. Then add 20 μL 0.2 M $CaCl_2$, and finally add 1 mL coagulation factor X, VIII, IX and XI deficient blood. The clotting time of coagulation factor X, VIII, IX and XI deficient blood was 4, 3.6, 4, 4 min, respectively. The coagulation effect of thrombin in the thrombin/zeolite composite is decreased (FIG. 4).
Preparation of thrombin/zeolite A composite 2: Zeolite A (Na type, the number of monovalent sodium ions accounts for 100% of the total number of the metal cations outside the zeolite framework) with microporous channels with the atomic ratio of silicon to aluminum of 2 was impregnated with a 5 M magnesium chloride solution at room temperature for 12 h to obtain the zeolite A. Disperse the zeolite A in the aqueous solution to form a suspension of the zeolite A; mix the suspension of zeolite A and trypsin at 25° C. for 30 min (the mass ratio of thrombin to zeolite A is 1:10) to make thrombin adsorb on the surface of zeolite A; and dry the above solution in vacuum at −20° C. for 5 h to obtain the thrombin/zeolite A composite 2.

The coagulation effect of thrombin/zeolite composite 2 was performed in normal blood and coagulation factor X, VIII, IX and XI deficient blood, and the clotting time was 2, 5, 5, 5.5 and 5.2 min, respectively.

From the comparison of Comparative Example 4 and Comparative Example 5, it can be seen that the coagulation time of the composite formed by the combination of thrombin and zeolite is longer than that of thrombin alone, that is, the corresponding coagulation effect is lower than that of thrombin alone. The performance of the composite of two hemostatic materials is not better than that of the single hemostatic material (Table 1).

Example 1

Preparation of Trypsin/Zeolite A Hemostatic Composition:
(1) Zeolite A (Na type, the number of monovalent sodium ions accounts for 100% of the total number of the metal cations outside the zeolite framework) with the atomic ratio of silicon to aluminum of 2 was impregnated with a 5 M magnesium chloride solution at room temperature for 12 h to obtain the zeolite A. The Zeolite A contains divalent magnesium ions and the number of divalent magnesium ions accounts for 95% of the total number of the metal cations outside the zeolite framework, and the number of monovalent sodium ions accounts for 5%.
(2) Disperse the 25 mg of zeolite A in the 1 mL aqueous solution to form a suspension of the zeolite A; mix the suspension of zeolite A and trypsin at 25° C. for 30 min (the mass ratio of trypsin to zeolite A is 1:10) to make trypsin adsorb on the surface of zeolite A; and dry the above solution in vacuum at −20° C. for 5 h to obtain the trypsin/zeolite A hemostatic composition.

The natural coagulation time of the trypsin/zeolite A hemostatic composition is 0.4 min, and the clotting time of coagulation factor X, VIII, IX, XI deficient blood is 0.5, 0.4, 0.4 and 0.45 min, respectively, which shows that the trypsin/zeolite A hemostatic composition has a procoagulant effect in both normal blood and coagulation factor X, VIII, IX, XI deficient blood. The trypsin/zeolite A hemostatic composition can promote coagulation for patients with hemophilia. As a control, when the zeolite A was added into all above-mentioned deficient blood, all the blood did not coagulate for a long time (Table 1).

From the comparison between Example 1 and Comparative Examples 2 and 3, it can be seen that the coagulation effect of the trypsin/zeolite A hemostatic composition is far better than that of the zeolite A or trypsin (FIG. 3), and the coagulation time is greatly shortened. The zeolite (pore structure and metal cations) in the hemostatic composition of the present disclosure positively regulates the spatial orientation of trypsin, so that the trypsin on the surface of the zeolite promotes the conversion of prothrombin into prothrombin in the clotting cascade. The procoagulant activity of the trypsin/zeolite A hemostatic composition is better than that of trypsin alone and zeolite alone. In the event of sudden and unexpected bleeding, it can stop bleeding very efficiently, decrease the risk of death from aortic bleeding, and reduce the damage of vital organs. The coagulation effect of the hemostatic composition is equivalent to that of thrombin, which can greatly reduce the cost of hemostatic materials and has more commercial prospects.

TABLE 1

The clotting time of trypsin/zeolite A hemostatic composition, trypsin and zeolite A

|  | Normal blood (min) | Coagulation factor X deficient blood (min) | Coagulation factor VIII deficient blood (min) | Coagulation factor IX deficient blood (min) | Coagulation factor XI deficient blood (min) |
| --- | --- | --- | --- | --- | --- |
| Trypsin/zeolite A hemostatic composition | 0.4 | 0.5 | 0.4 | 0.4 | 0.45 |
| Zeolite A | 2.8 | No blood clot | No blood clot | No blood clot | No blood clot |
| Trypsin | 4 | 4 | 4.6 | 4 | 4 |
| Thrombin | 0.5 | 0.5 | 0.52 | 0.51 | 0.54 |
| Thrombin/zeolite composite | 2.2 | 4 | 3.6 | 4 | 4 |

Example 2

Preparation of Trypsin/Zeolite A Hemostatic Composition with Different Divalent Metal Ions:

(1) Zeolite A (Na type) with microporous channels and the atomic ratio of silicon to aluminum of 2 is impregnated with a 5 M cobalt chloride, nickel chloride, calcium chloride, magnesium chloride or strontium chloride solution at room temperature for 12 h to obtain zeolite A with different divalent metal ions.

(2) Disperse the 25 mg of zeolite A with different divalent metal ions in the 1 mL aqueous solution to form a suspension of the zeolite A; mix the suspension of zeolite A and trypsin at 25° C. for 30 min (the mass ratio of trypsin to zeolite A is 1:10) to make trypsin adsorb on the surface of zeolite A; and dry the above solution in vacuum at −20° C. for 5 h to obtain the trypsin/zeolite A hemostatic composition with different divalent metal ions.

The coagulation effect of the trypsin/zeolite A hemostatic composition with different divalent metal ions (cobalt, nickel, calcium, magnesium, strontium) and Comparative Examples 1-3 are compared (Table 2). Trypsin/zeolite A hemostatic composition with divalent metal ions is much better than that of natural coagulation, trypsin and zeolite A. The coagulation effect of trypsin/zeolite A hemostatic composition in coagulation factor X, VIII, IX, XI deficient blood is also great, and the coagulation time is greatly shortened.

TABLE 2

The clotting time of trypsin/zeolite A hemostatic composition with different divalent metal ions

|  | Content of divalent metal ions | Content of monovalent cation | Normal blood (min) | Coagulation factor X deficient blood (min) | Coagulation factor VIII deficient blood (min) | Coagulation factor IX deficient blood (min) | Coagulation factor XI deficient blood (min) |
| --- | --- | --- | --- | --- | --- | --- | --- |
| Trypsin/Co-zeolite A hemostatic composition | 65% | 35% | 0.4 | 0.5 | 0.4 | 0.4 | 0.45 |
| Trypsin/Ni-zeolite A hemostatic composition | 70% | 30% | 0.35 | 0.35 | 0.34 | 0.36 | 0.35 |
| Trypsin/Ca-zeolite A hemostatic composition | 90% | 10% | 0.45 | 0.3 | 0.4 | 0.4 | 0.35 |
| Trypsin/Mg-zeolite A hemostatic composition | 95% | 5% | 0.4 | 0.5 | 0.4 | 0.4 | 0.45 |
| Trypsin/Sr-zeolite A hemostatic composition | 72% | 28% | 0.42 | 0.45 | 0.46 | 0.42 | 0.45 |
| Trypsin/Co-Ni-zeolite A hemostatic composition | 50% | 50% | 0.4 | 0.45 | 0.45 | 0.46 | 0.42 |

TABLE 2-continued

The clotting time of trypsin/zeolite A hemostatic composition with different divalent metal ions

| | Content of divalent metal ions | Content of monovalent cation | Normal blood (min) | Coagulation factor X deficient blood (min) | Coagulation factor VIII deficient blood (min) | Coagulation factor IX deficient blood (min) | Coagulation factor XI deficient blood (min) |
|---|---|---|---|---|---|---|---|
| Trypsin/Co-Ca-zeolite A hemostatic composition | 80% | 20% | 0.42 | 0.35 | 0.4 | 0.36 | 0.45 |
| Trypsin/Ca-Mg-zeolite A hemostatic composition | 80% | 20% | 0.35 | 0.5 | 0.4 | 0.4 | 0.45 |
| Trypsin/Sr-Mg-zeolite A hemostatic composition | 78% | 22% | 0.35 | 0.38 | 0.36 | 0.4 | 0.45 |
| Trypsin/Sr-Ni-zeolite A hemostatic composition | 60% | 40% | 0.45 | 0.38 | 0.35 | 0.4 | 0.45 |

Remarks: 1) Trypsin/Co-zeolite A hemostatic composition is defined as a hemostatic composition containing trypsin and zeolite A with cobalt divalent metal ions; 2) Trypsin/Co—Ni-zeolite A hemostatic composition is defined as a hemostatic composition containing trypsin and zeolite with cobalt and nickel divalent metal ions; 3) The monovalent cation in the Table 2 is sodium ion.

In some embodiments, the monovalent cation of zeolite A in Example 2 is selected from the group consisting of sodium ion, potassium ion, lithium ion, ammonium ion, and hydrogen ion. When the monovalent cation described in Example 2 is replaced with any one or more of potassium ion, lithium ion, ammonium ion, and hydrogen ion, and trypsin/zeolite A hemostatic composition containing divalent metal cations can achieve the coagulation effect of the present disclosure.

Example 3

Preparation of Trypsin/Zeolite A Hemostatic Composition with Different Mass Ratios of Trypsin to Zeolite:

(1) Zeolite A with microporous channels and the atomic ratio of silicon to aluminum of 2 is impregnated with a 5 M magnesium chloride solution at room temperature for 12 h to obtain the zeolite A. The Zeolite A contains divalent magnesium ions and the number of divalent magnesium ions accounts for 95% of the total number of the metal cations outside the zeolite framework, and the number of monovalent sodium ions accounts for 5%.

(2) Disperse the 25 mg of zeolite A with different divalent metal ions in the 1 mL aqueous solution to form a suspension of the zeolite A; mix the suspension of zeolite A and trypsin at 25° C. for 30 min (the mass ratio of trypsin to zeolite A is 1:200, 1:100, 1:60, 1:50, 1:40, 1:20, 1:10, 1.5:10, 2:10, 2.5:10, 3:10, 4:10) to make trypsin adsorb on the surface of zeolite; and dry the above solution in vacuum at −20° C. for 5 h to obtain the trypsin/zeolite A hemostatic composition with different mass ratios (Table 3).

TABLE 3

The clotting time of trypsin/zeolite A hemostatic composition with different mass ratios

| Trypsin/ zeolite A hemostatic composition with different mass ratios | Normal blood (min) | Coagulation factor X deficient blood (min) | Coagulation factor VIII deficient blood (min) | Coagulation factor IX deficient blood (min) | Coagulation factor XI deficient blood (min) |
|---|---|---|---|---|---|
| 1:200 | 0.5 | 0.45 | 0.46 | 0.42 | 0.45 |
| 1:100 | 0.5 | 0.45 | 0.45 | 0.46 | 0.42 |
| 1:60 | 0.45 | 0.45 | 0.45 | 0.46 | 0.42 |
| 1:50 | 0.42 | 0.35 | 0.4 | 0.36 | 0.45 |
| 1:40 | 0.42 | 0.5 | 0.4 | 0.4 | 0.45 |
| 1:20 | 0.4 | 0.35 | 0.4 | 0.36 | 0.45 |
| 1:10 | 0.4 | 0.5 | 0.4 | 0.4 | 0.4 |
| 1.5:10 | 0.35 | 0.5 | 0.4 | 0.4 | 0.45 |
| 2:10 | 0.35 | 0.38 | 0.36 | 0.4 | 0.4 |
| 2.5:10 | 0.4 | 0.38 | 0.35 | 0.4 | 0.45 |
| 3:10 | 0.4 | 0.38 | 0.36 | 0.4 | 0.4 |
| 4:10 | 0.5 | 0.5 | 0.4 | 0.4 | 0.45 |

The coagulation effect of trypsin/zeolite A hemostatic composition with different mass ratios (mass ratio of 1:200, 1:100, 1:60, 1:50, 1:40, 1:20, 1:10, 1.5:10, 2:10, 2.5:10, 3:10, 4:10) and Comparative Examples 1-3 were compared. In the range of the mass ratio of trypsin to zeolite of 1:200 to 4:10, the coagulation effect of trypsin/zeolite A hemostatic composition is much better than that of natural coagulation, trypsin and zeolite (Table 3). The coagulation effect of trypsin/zeolite A hemostatic composition in blood lacking coagulation factors X, VIII, IX and XI is also great, and the coagulation time is greatly shortened.

Comparative Example 6

(1) Zeolite A (Na type) with microporous channels and the atomic ratio of silicon to aluminum of 2 is impregnated with 5 M sodium chloride solution at room temperature for 24 h to obtain the zeolite A (zeolite 4A) whose metal cation outside the zeolite framework is sodium ion. And the number of monovalent sodium ion accounts for 100% of the total number of the metal cations outside the zeolite framework.

(2) Disperse the 25 mg of zeolite 4A in the 1 mL aqueous solution to form a suspension of the zeolite 4A; mix the suspension of zeolite 4A and trypsin at 25° C. for 30 min (the mass ratio of trypsin to zeolite 4A is 1:10) to make trypsin adsorb on the surface of zeolite; and dry the above solution in vacuum at −20° C. for 5 h to obtain the trypsin/zeolite 4A composition.

The natural coagulation time of the trypsin/zeolite 4A composition is 5 min, and the clotting time of the coagulation factor X, VIII, IX, XI deficient blood is 6.5, 6, 6, and 6.5 min, respectively. This shows that trypsin/zeolite 4A composition is not ideal in the normal blood and coagulation factor X, VIII, IX, XI deficient blood.

Figure 5:
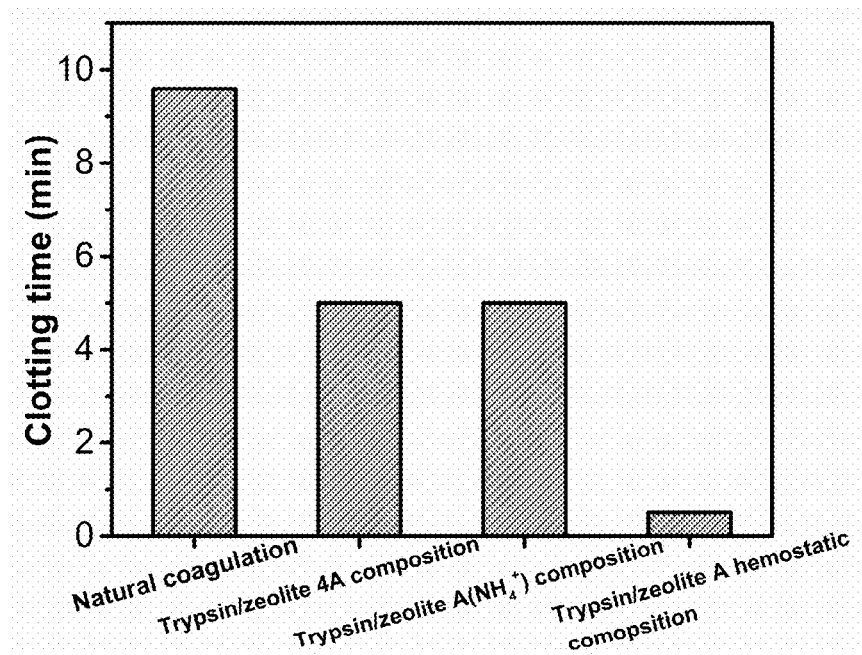
FIG. 5 is a comparison diagram of the coagulation effect of natural coagulation, trypsin/zeolite 4A composition, trypsin/zeolite A ($NH_4^+$) composition, and trypsin/zeolite A hemostatic composition of the present disclosure.

The comparison between Example 1 and Comparative Example 6 shows that the coagulation effect of the trypsin/zeolite 4A composition is far inferior to that of the trypsin/zeolite A hemostatic composition (FIG. 5), and the trypsin/zeolite A hemostatic composition is even worse than zeolite 4A or trypsin. The trypsin on the zeolite 4A (without divalent metal ions) is reduced, or even completely inactivated. It also leads to a decrease in the procoagulant effect of zeolite.

Wherein, when the metal cations outside the zeolite framework are all monovalent cations (the content of monovalent cations is 100%), the composition formed by zeolite and trypsin has low procoagulant activity and does not belong to the hemostatic composition of the present disclosure.

The monovalent cations are selected from the group consisting of sodium ion, potassium ion, lithium ion, ammonium ion and hydrogen ion.

Comparative Example 7

(1) Zeolite A (Na type) with microporous channels and the atomic ratio of silicon to aluminum of 2 is impregnated with 5 M ammonium chloride solution at room temperature for 24 h to obtain the zeolite A containing monovalent ammonium ion and sodium ion. The number of monovalent ammonium ion accounts for 60% of the total number of the metal cations outside the zeolite framework; and the number of monovalent sodium ion accounts for 40% of the total number of the metal cations outside the zeolite framework.

(2) Disperse the zeolite A ($NH_4^+$) in 1 mL of aqueous solution to form a suspension of zeolite A ($NH_4^+$); mix the suspension of zeolite A ($NH_4^+$) and trypsin at 25° C. for 30 min (the mass ratio of trypsin to zeolite A ($NH_4^+$) is 1:10) to make trypsin adsorb on the surface of zeolite; and dry the above solution in vacuum at −20° C. for 5 h to obtain the trypsin/zeolite A ($NH_4^+$) composition.

The natural coagulation time of the trypsin/zeolite A ($NH_4^+$) composition is 5.2 min, and the clotting time of the coagulation factor X, VIII, IX, XI deficient blood is 6.1, 6.4, 6.4, 6.5 min, respectively. This shows that trypsin/zeolite A ($NH_4^+$) composition is not ideal in the normal blood and coagulation factor X, VIII, IX, XI deficient blood.

The comparison between Example 1 and Comparative Example 7 shows that the coagulation effect of the trypsin/zeolite A ($NH_4^+$) composition is far inferior to that of the trypsin/zeolite A hemostatic composition (FIG. 5), and the trypsin/zeolite A ($NH_4^+$) composition is even worse than zeolite A ($NH_4^+$, 2.8 min) or trypsin. The activity of trypsin on the zeolite A ($NH_4^+$, without divalent metal ions) is reduced, or even completely inactivated. It also leads to a decrease in the procoagulant effect of zeolite.

Comparative Example 8

(1) The zeolite β (Na type) with microporous channels and the atomic ratio of silicon to aluminum of 15 is impregnated with 0.1 M ammonia solution at room temperature for 24 h to obtain the zeolite β containing monovalent ammonium ion and sodium ion. The number of monovalent ammonium ion accounts for 40% of the total number of the metal cations outside the zeolite framework; and the number of monovalent sodium ion accounts for 60% of the total number of the metal cations outside the zeolite framework.

(2) Disperse the zeolite α ($NH_4^+$) in 1 mL of aqueous solution to form a suspension of zeolite β ($NH_4^+$); mix the suspension of zeolite α ($NH_4^+$) and trypsin at 25° C. for 30 min (the mass ratio of trypsin to zeolite β ($NH_4^+$) is 1:10) to make trypsin adsorb on the surface of zeolite; and dry the above solution in vacuum at −20° C. for 5 h to obtain the trypsin/zeolite β ($NH_4^+$) composition.

The natural coagulation time of the trypsin/zeolite β ($NH_4^+$) composition is 5.6 min, and the clotting time of the coagulation factor X, VIII, IX, XI deficient blood is 6.1, 6.4, 6.3, 6.5 min, respectively. This shows that trypsin/zeolite β ($NH_4^+$) composition is not ideal in the normal blood and coagulation factor X, VIII, IX, XI deficient blood. The coagulation effect of the trypsin/zeolite β ($NH_4^+$) composition is far inferior to that of the trypsin/zeolite hemostatic composition of present disclosure, and the trypsin/zeolite β ($NH_4^+$) composition is even worse than zeolite β $NH_4+$, 2.8 min) or trypsin. The trypsin on the zeolite β ($NH_4^+$, without divalent metal ions) is reduced, or even completely inactivated. It also leads to a decrease in the procoagulant effect of zeolite.

Comparative Example 9

(1) Zeolite A (Na type) with microporous channels and the atomic ratio of silicon to aluminum of 2 is impregnated with a 5 M magnesium chloride solution at room temperature for 12 h to obtain zeolite A with divalent magnesium ions. The number of divalent magnesium ions accounts for 95% of the total number of the metal cations outside the zeolite framework, and the number of monovalent sodium ions accounts for 5%.

(2) Disperse the 25 mg of zeolite A in the 1 mL aqueous solution to form a suspension of the zeolite A; mix the suspension of zeolite A and 0.83 mg of trypsin at 25° C. for 30 min (the mass ratio of trypsin to zeolite A is 1:300) to make trypsin adsorb on the surface of zeolite A; and dry the above solution in vacuum at −20° C. for 5 h to obtain the trypsin/zeolite A composition (1:300).

The natural coagulation time of the trypsin/zeolite A composition (1:300) was 2.8 min, and the coagulation factor X, VIII, IX, XI deficient blood did not coagulate for a long time. It can be seen that the ratio of zeolite A to trypsin should in a specific range to play a better procoagulant effect. When the ratio of trypsin to zeolite is less than 1:200, the procoagulant effect is poor.

Comparative Example 10

(1) Zeolite A (Na type) with microporous channels and the atomic ratio of silicon to aluminum of 2 is impregnated with a 5 M magnesium chloride solution at room temperature for 12 h to obtain zeolite A with divalent magnesium ions. The number of divalent magnesium ions accounts for 95% of the total number of the metal cations outside the zeolite framework, and the number of monovalent sodium ions accounts for 5%.

(2) Disperse the 25 mg of zeolite A in the 1 mL aqueous solution to form a suspension of the zeolite A; mix the suspension of zeolite A and trypsin at 25° C. for 30 min (the mass ratio of trypsin to zeolite A is 5:10) to make trypsin adsorb on the surface of zeolite A; and dry the above solution in vacuum at −20° C. for 5 h to obtain the trypsin/zeolite A composition (5:10).

The natural blood and coagulation factor X, VIII, IX, XI deficient blood did not coagulate for a long time after adding the trypsin/zeolite A composition (5:10). It can be seen that the mass ratio of zeolite A to trypsin should in a specific range to play a better procoagulant effect. When the mass ratio of trypsin to zeolite is less than 1:200, the procoagulant effect is poor. When the mass ratio of trypsin to zeolite is higher than 4:10, it will cause the blood become anticoagulation, and aggravate the massive loss of blood.

From the comparison between Example 1 and Comparative Examples 3, 9 and 10, it can be obtained that the mass ratio of zeolite to trypsin in the composition of the present disclosure needs to meet a specific mass ratio range (1:200-4:10) When the mass ratio of the two is outside the specific range (Comparative Example 9, Comparative Example 10), the coagulation time of the composite of zeolite and trypsin is longer than that of trypsin alone. That is, the procoagulant activity is lower than that of trypsin alone, and the highly effective hemostatic performance of the present disclosure cannot be achieved.

Comparative Example 11

Disperse the mesoporous silica MCM-41 (pores of 2.8-4.5 nm) in the 1 mL aqueous solution to form a suspension of the mesoporous silica MCM-41; mix the suspension of mesoporous silica MCM-41 and trypsin at 25° C. for 30 min (the mass ratio of trypsin to mesoporous silica MCM-41 is 1:10) to make trypsin adsorb on the surface of mesoporous silica MCM-41; and dry the above solution in vacuum at −20° C. for 5 h to obtain the trypsin/MCM-41 composition.

The natural coagulation time of the trypsin/MCM-41 composition was 5 min, and the clotting time of the coagulation factor X, VIII, IX, XI deficient blood is 5.5, 6.3, 6.2, 6.1 min, respectively. This shows that the procoagulant effect of trypsin/MCM-41 composition is not ideal in the normal blood and coagulation factor X, VIII, IX, XI deficient blood. And the trypsin/MCM-41 composition is even worse than MCM-41 (3 min) or trypsin.

Comparative Example 12

Mesoporous Zeolite A (Na type, pores of 5 nm) with the atomic ratio of silicon to aluminum of 2 is impregnated with a 5 M magnesium chloride solution at room temperature for 12 h to obtain zeolite A with divalent magnesium ions. The number of divalent magnesium ions accounts for 95% of the total number of the metal cations outside the zeolite framework, and the number of monovalent sodium ions accounts for 5%.

Disperse the mesoporous zeolite A in the 1 mL aqueous solution to form a suspension of the mesoporous zeolite A; mix the suspension of mesoporous zeolite A and trypsin at 25° C. for 30 min (the mass ratio of trypsin to mesoporous zeolite A is 1:10) to make trypsin adsorb on the surface of mesoporous zeolite A; and dry the above solution in vacuum at −20° C. for 5 h to obtain the trypsin/mesoporous zeolite A composition.

The natural coagulation time of the trypsin/mesoporous zeolite A composition was 5.5 min, and the clotting time of the coagulation factor X, VIII, IX, XI deficient blood is 5.6, 5.3, 5.2, 5.1 min, respectively. This shows that trypsin/ mesoporous zeolite A composition is not ideal in the normal blood and coagulation factor X, VIII, IX, XI deficient blood. The coagulation effect of the trypsin/mesoporous zeolite A composition is even worse than mesoporous zeolite A or trypsin.

From the comparison between Example 1 and Comparative Examples 11, 12, the procoagulant effect of the trypsin/ mesoporous zeolite composition is lower than that of the trypsin/zeolite hemostatic composition of the present disclosure, and the trypsin/mesoporous zeolite composition is less effective than mesoporous zeolite or trypsin alone. Under the conditions of the same mass ratio of zeolite to trypsin and the same contents of divalent metal cation, the pore size of the zeolite plays a key role in the hemostatic performance of the hemostatic composition composed of zeolite and trypsin. This is because trypsin enters the mesopores of the mesoporous zeolite, and biomacromolecules cannot enter the mesoporous pores of the zeolite; when contacting blood, the trypsin in the mesoporous pores cannot contact the coagulation factors of the clotting cascade in the blood, cannot quickly activate the clotting cascade, so that the procoagulant effect is reduced.

The pore size of the zeolite mesopores of the present disclosure is less than 50 nm and larger than the size of the micropores.

Comparative Example 13

(1) Chabazite (Na type) with microporous channels and the atomic ratio of silicon to aluminum of 1.5 is impregnated with a 5 M magnesium chloride solution at room temperature for 12 h to obtain the chabazite. The chabazite contains divalent magnesium ions and the number of divalent magnesium ions accounts for 95% of the total number of the metal cations outside the zeolite framework, and the number of monovalent sodium ions accounts for 5%.

(2) Evaluation of the coagulation effect of the chabazite prepared above: take 25 mg of the chabazite into a 2 mL centrifuge tube, perform an in vitro coagulation experiment at 37° C., and heat the normal blood at 37° C. for half an hour. Then, add 20 μL of 0.2 M $CaCl_2$, and finally add 1 mL of normal blood. The clotting time is recorded as the coagulation time of chabazite (2 min), which shows that coagulation effect of chabazite is ordinary.

Take 25 mg of chabazite and add it to a 2 mL centrifuge tube, perform an in vitro coagulation experiment at 37° C., and heat the coagulation factor X, VIII, IX and XI deficient blood at 37° C. for half an hour. Then add 20 μL 0.2 M $CaCl_2$, and finally add 1 mL coagulation factor X, VIII, IX and XI deficient blood. The clotting time is recorded as the coagulation time of chabazite. However, all above-mentioned deficient blood did not coagulate for a long time, which shows that chabazite has no procoagulant effect on patients with hemophilia.

Example 4

Preparation of Trypsin/Chabazite Hemostatic Composition:

(1) Chabazite (Na type) with microporous channels and the atomic ratio of silicon to aluminum of 1.5 is impregnated with a 5 M magnesium chloride solution at room temperature for 12 h to obtain the chabazite. The chabazite contains divalent magnesium ions and the number of divalent magnesium ions accounts for 95% of the total number of the metal cations outside the zeolite framework, and the number of monovalent sodium ions accounts for 5%.

(2) Disperse the 25 mg of chabazite in the 1 mL aqueous solution to form a suspension of the chabazite; mix the suspension of chabazite and trypsin at 25° C. for 30 min (the mass ratio of trypsin to chabazite is 1:10) to make trypsin adsorb on the surface of zeolite; and dry the above solution in vacuum at −20° C. for 5 h to obtain the trypsin/chabazite hemostatic composition.

The natural coagulation time of the trypsin/chabazite hemostatic composition is 0.35 min, and the clotting time of coagulation factor X, VIII, IX, XI deficient blood is 0.45, 0.35, 0.35 and 0.45 min, respectively, which shows that the trypsin/chabazite hemostatic composition has a procoagulant effect in both normal blood and coagulation factor X, VIII, IX, XI deficient blood, and the clotting time is greatly shortened. The trypsin/chabazite hemostatic composition can promote coagulation for patients with hemophilia. As a control, when the chabazite was added into all above-mentioned deficient blood, all the blood did not coagulate for a long time. From the comparison between Example 4 and Comparative Examples 13, it can be seen that the coagulation effect of the trypsin/chabazite hemostatic composition is far better than that of the chabazite or trypsin, and the coagulation time is greatly shortened.

Comparative Example 14

(1) The zeolite β (Na type) with microporous channels and the atomic ratio of silicon to aluminum of 15 is impregnated with a 5 M magnesium chloride solution at room temperature for 12 h to obtain the zeolite β. The zeolite β contains divalent magnesium ions and the number of divalent magnesium ions accounts for 95% of the total number of the metal cations outside the zeolite framework, and the number of monovalent sodium ions accounts for 5%.

(2) Evaluation of the coagulation effect of the zeolite β prepared above: take 25 mg of the zeolite α into a 2 mL centrifuge tube, perform an in vitro coagulation experiment at 37° C., and heat the normal blood at 37° C. for half an hour. Then, add 20 μL of 0.2 M $CaCl_2$, and finally add 1 mL of normal blood. The clotting time is recorded as the coagulation time of zeolite β (3 min), which shows that coagulation effect of zeolite β is ordinary.

Take 25 mg of zeolite β and add it to a 2 mL centrifuge tube, perform an in vitro coagulation experiment at 37° C., and heat the coagulation factor X, VIII, IX and XI deficient blood at 37° C. for half an hour. Then add 20 μL 0.2 M $CaCl_2$, and finally add 1 mL coagulation factor X, VIII, IX and XI deficient blood. The clotting time is recorded as the coagulation time of zeolite β. However, all above-mentioned deficient blood did not coagulate for a long time, which shows that zeolite β has no procoagulant effect on patients with hemophilia.

Example 5

Preparation of Trypsin/Zeolite β Hemostatic Composition:

(1) The zeolite β (Na type) with microporous channels and the atomic ratio of silicon to aluminum of is impregnated with a 5 M magnesium chloride solution at room temperature for 12 h to obtain the zeolite β. The zeolite β contains divalent magnesium ions and the number of divalent magnesium ions accounts for 95% of the total number of the metal cations outside the zeolite framework, and the number of monovalent sodium ions accounts for 5%.

(2) Disperse the 25 mg of zeolite β in the 1 mL aqueous solution to form a suspension of the zeolite β; mix the suspension of zeolite β and trypsin at 25° C. for 30 min (the mass ratio of trypsin to zeolite β is 1:10) to make trypsin adsorb on the surface of zeolite; and dry the above solution in vacuum at −20° C. for 5 h to obtain the trypsin/zeolite β hemostatic composition.

The natural coagulation time of the trypsin/zeolite β hemostatic composition is 0.52 min, and the clotting time of coagulation factor X, VIII, IX, XI deficient blood is 0.55, 0.55, 0.5 and 0.5 min, respectively, which shows that the trypsin/zeolite β hemostatic composition has a procoagulant effect in both normal blood and coagulation factor X, VIII, IX, XI deficient blood, and the clotting time is greatly shortened. The trypsin/zeolite β hemostatic composition can promote coagulation for patients with hemophilia. As a control, when the zeolite β was added into all above-mentioned deficient blood, all the blood did not coagulate for a long time. From the comparison between Example 5 and Comparative Examples 14, it can be seen that the coagulation effect of the trypsin/zeolite β hemostatic composition is far better than that of the zeolite β or trypsin, and the coagulation time is greatly shortened.

Comparative Example 15

(1) The mordenite (Na type) with microporous channels and the atomic ratio of silicon to aluminum of 10 is impregnated with a 5 M magnesium chloride solution at room temperature for 12 h to obtain the mordenite. The mordenite contains divalent magnesium ions and the number of divalent magnesium ions accounts for 95% of the total number of the metal cations outside the zeolite framework, and the number of monovalent sodium ions accounts for 5%.

(2) Evaluation of the coagulation effect of the mordenite prepared above: take 25 mg of the mordenite into a 2 mL centrifuge tube, perform an in vitro coagulation experiment at 37° C., and heat the normal blood at 37° C. for half an hour. Then, add 20 μL of 0.2 M $CaCl_2$, and finally add 1 mL of normal blood. The clotting time is recorded as the coagulation time of mordenite (2.5 min), which shows that coagulation effect of mordenite is ordinary.

Take 25 mg of mordenite and add it to a 2 mL centrifuge tube, perform an in vitro coagulation experiment at 37° C., and heat the coagulation factor X, VIII, IX and XI deficient blood at 37° C. for half an hour. Then add 20 μL 0.2 M $CaCl_2$, and finally add 1 mL coagulation factor X, VIII, IX and XI deficient blood. The clotting time is recorded as the coagulation time of mordenite. However, all above-mentioned deficient blood did not coagulate for a long time, which shows that mordenite has no procoagulant effect on patients with hemophilia.

Example 6

Preparation of Trypsin/Mordenite Hemostatic Composition:

(1) The mordenite (Na type) with microporous channels and the atomic ratio of silicon to aluminum of 10 is impregnated with a 5 M magnesium chloride solution at room temperature for 12 h to obtain the mordenite. The mordenite contains divalent magnesium ions and the number of divalent magnesium ions accounts for 95% of the total number of the metal cations outside the zeolite framework, and the number of monovalent sodium ions accounts for 5%.

(2) Disperse the 25 mg of mordenite in the 1 mL aqueous solution to form a suspension of the mordenite; mix the suspension of mordenite and trypsin at 25° C. for 30 min (the mass ratio of trypsin to mordenite is 1:10) to make trypsin adsorb on the surface of zeolite; and dry the above solution in vacuum at −20° C. for 5 h to obtain the trypsin/mordenite hemostatic composition.

The natural coagulation time of the trypsin/mordenite hemostatic composition is 0.45 min, and the clotting time of coagulation factor X, VIII, IX, XI deficient blood is 045, 0.45, 0.5 and 0.5 min, respectively, which shows that the trypsin/mordenite hemostatic composition has a procoagulant effect in both normal blood and coagulation factor X, VIII, IX, XI deficient blood, and the clotting time is greatly shortened. The trypsin/mordenite hemostatic composition can promote coagulation for patients with hemophilia. As a control, when the mordenite was added into all above-mentioned deficient blood, all the blood did not coagulate for a long time. From the comparison between Example 6 and Comparative Examples 15, it can be seen that the coagulation effect of the trypsin/mordenite hemostatic composition is far better than that of the mordenite or trypsin, and the coagulation time is greatly shortened.

Comparative Example 16

(1) The zeolite X (Na type) with microporous channels and the atomic ratio of silicon to aluminum of 1 is impregnated with a 5 M magnesium chloride solution at room temperature for 12 h to obtain the zeolite X. The zeolite X contains divalent magnesium ions and the number of divalent magnesium ions accounts for 95% of the total number of the metal cations outside the zeolite framework, and the number of monovalent sodium ions accounts for 5%.

(2) Evaluation of the coagulation effect of the zeolite X prepared above: take 25 mg of the zeolite X into a 2 mL centrifuge tube, perform an in vitro coagulation experiment at 37° C., and heat the normal blood at 37° C. for half an hour. Then, add 20 μL of 0.2 M $CaCl_2$, and finally add 1 mL of normal blood. The clotting time is recorded as the coagulation time of zeolite X (2.1 min), which shows that coagulation effect of zeolite X is ordinary.

Take 25 mg of zeolite X and add it to a 2 mL centrifuge tube, perform an in vitro coagulation experiment at 37° C., and heat the coagulation factor X, VIII, IX and XI deficient blood at 37° C. for half an hour. Then add 20 μL 0.2 M $CaCl_2$, and finally add 1 mL coagulation factor X, VIII, IX and XI deficient blood. The clotting time is recorded as the coagulation time of zeolite X. However, all above-mentioned deficient blood did not coagulate for a long time, which shows that zeolite X has no procoagulant effect on patients with hemophilia.

Example 7

Preparation of Trypsin/Zeolite X Hemostatic Composition:

(1) The zeolite X (Na type) with microporous channels and the atomic ratio of silicon to aluminum of 1 is impregnated with a 5 M magnesium chloride solution at room temperature for 12 h to obtain the zeolite X. The zeolite X contains divalent magnesium ions and the number of divalent magnesium ions accounts for 95% of the total number of the metal cations outside the zeolite framework, and the number of monovalent sodium ions accounts for 5%.

(2) Disperse the 25 mg of zeolite X in the 1 mL aqueous solution to form a suspension of the zeolite X; mix the suspension of zeolite X and trypsin at 25° C. for 30 min (the mass ratio of trypsin to zeolite X is 1:10) to make trypsin adsorb on the surface of zeolite; and dry the above solution in vacuum at −20° C. for 5 h to obtain the trypsin/zeolite X hemostatic composition.

The natural coagulation time of the trypsin/zeolite X hemostatic composition is 0.48 min, and the clotting time of coagulation factor X, VIII, IX, XI deficient blood is 0.48, 0.45, 0.5 and 0.5 min, respectively, which shows that the trypsin/zeolite X hemostatic composition has a procoagulant effect in both normal blood and coagulation factor X, VIII, IX, XI deficient blood, and the clotting time is greatly shortened. The trypsin/zeolite X hemostatic composition can promote coagulation for patients with hemophilia. As a control, when the zeolite X was added into all above-mentioned deficient blood, all the blood did not coagulate for a long time. From the comparison between Example 7 and Comparative Examples 16, it can be seen that the coagulation effect of the trypsin/zeolite X hemostatic composition is far better than that of the zeolite X or trypsin, and the coagulation time is greatly shortened.

Comparative Example 17

(1) The zeolite Y (Na type) with microporous channels and the atomic ratio of silicon to aluminum of 3 is impregnated with a 5 M magnesium chloride solution at room temperature for 12 h to obtain the zeolite Y. The zeolite Y contains divalent magnesium ions and the number of divalent magnesium ions accounts for 95% of the total number of the metal cations outside the zeolite framework, and the number of monovalent sodium ions accounts for 5%.

(2) Evaluation of the coagulation effect of the zeolite Y prepared above: take 25 mg of the zeolite Y into a 2 mL centrifuge tube, perform an in vitro coagulation experiment at 37° C., and heat the normal blood at 37° C. for half an hour. Then, add 20 μL of 0.2 M $CaCl_2$, and finally add 1 mL of normal blood. The clotting time is recorded as the coagulation time of zeolite Y (2 min), which shows that coagulation effect of zeolite Y is ordinary.

Take 25 mg of zeolite Y and add it to a 2 mL centrifuge tube, perform an in vitro coagulation experiment at 37° C., and heat the coagulation factor X, VIII, IX and XI deficient blood at 37° C. for half an hour. Then add 20 μL 0.2 M $CaCl_2$, and finally add 1 mL coagulation factor X, VIII, IX and XI deficient blood. The clotting time is recorded as the coagulation time of zeolite Y. However, all above-mentioned deficient blood did not coagulate for a long time, which shows that zeolite Y has no procoagulant effect on patients with hemophilia.

Example 8

Preparation of Trypsin/Zeolite Y Hemostatic Composition:

(1) The zeolite Y (Na type) with microporous channels and the atomic ratio of silicon to aluminum of 3 is impregnated with a 5 M magnesium chloride solution at room temperature for 12 h to obtain the zeolite Y. The zeolite Y contains divalent magnesium ions and the number of divalent magnesium ions accounts for 95% of the total number of the metal cations outside the zeolite framework, and the number of monovalent sodium ions accounts for 5%.

(2) Disperse the 25 mg of zeolite Y in the 1 mL aqueous solution to form a suspension of the zeolite Y; mix the suspension of zeolite Y and trypsin at 25° C. for 30 min (the mass ratio of trypsin to zeolite Y is 1:10) to make trypsin adsorb on the surface of zeolite; and dry the above solution in vacuum at −20° C. for 5 h to obtain the trypsin/zeolite Y hemostatic composition.

The natural coagulation time of the trypsin/zeolite Y hemostatic composition is 0.3 min, and the clotting time of coagulation factor X, VIII, IX, XI deficient blood is 0.33, 0.4, 0.3 and 0.3 min, respectively, which shows that the trypsin/zeolite Y hemostatic composition has a procoagulant effect in both normal blood and coagulation factor X, VIII, IX, XI deficient blood, and the clotting time is greatly shortened. The trypsin/zeolite Y hemostatic composition can promote coagulation for patients with hemophilia. As a control, when the zeolite Y was added into all above-mentioned deficient blood, all the blood did not coagulate for a long time. From the comparison between Example 8 and Comparative Examples 17, it can be seen that the coagulation effect of the trypsin/zeolite Y hemostatic composition is far better than that of the zeolite Y or trypsin, and the coagulation time is greatly shortened.

Comparative Example 18

(1) The zeolite ZSM-5 (Na type) with microporous channels and the atomic ratio of silicon to aluminum of 20 is impregnated with a 5 M magnesium chloride solution at room temperature for 12 h to obtain the zeolite ZSM-5. The zeolite ZSM-5 contains divalent magnesium ions and the number of divalent magnesium ions accounts for 95% of the total number of the metal cations outside the zeolite framework, and the number of monovalent sodium ions accounts for 5%.

(2) Evaluation of the coagulation effect of the zeolite ZSM-5 prepared above: take 25 mg of the zeolite ZSM-5 into a 2 mL centrifuge tube, perform an in vitro coagulation experiment at 37° C., and heat the normal blood at 37° C. for half an hour. Then, add 20 μL of 0.2 M $CaCl_2$, and finally add 1 mL of normal blood. The clotting time is recorded as the coagulation time of zeolite ZSM-5 (2 min), which shows that coagulation effect of zeolite ZSM-5 is ordinary.

Take 25 mg of zeolite ZSM-5 and add it to a 2 mL centrifuge tube, perform an in vitro coagulation experiment at 37° C., and heat the coagulation factor X, VIII, IX and XI deficient blood at 37° C. for half an hour. Then add 20 μL 0.2 M $CaCl_2$, and finally add 1 mL coagulation factor X, VIII, IX and XI deficient blood. The clotting time is recorded as the coagulation time of zeolite ZSM-5. However, all above-mentioned deficient blood did not coagulate for a long time, which shows that zeolite ZSM-5 has no procoagulant effect on patients with hemophilia.

Example 9

Preparation of Trypsin/Zeolite ZSM-5 Hemostatic Composition:

(1) The zeolite ZSM-5 (Na type) with microporous channels and the atomic ratio of silicon to aluminum of 20 is impregnated with a 5 M magnesium chloride solution at room temperature for 12 h to obtain the zeolite ZSM-5. The zeolite ZSM-5 contains divalent magnesium ions and the number of divalent magnesium ions accounts for 95% of the total number of the metal cations outside the zeolite framework, and the number of monovalent sodium ions accounts for 5%.

(2) Disperse the 25 mg of zeolite ZSM-5 in the 1 mL aqueous solution to form a suspension of the zeolite ZSM-5; mix the suspension of zeolite ZSM-5 and trypsin at 25° C. for 30 min (the mass ratio of trypsin to zeolite ZSM-5 is 1:10) to make trypsin adsorb on the surface of zeolite; and dry the above solution in vacuum at −20° C. for 5 h to obtain the trypsin/zeolite ZSM-5 hemostatic composition.

The natural coagulation time of the trypsin/zeolite ZSM-5 hemostatic composition is 0.4 min, and the clotting time of coagulation factor X, VIII, IX, XI deficient blood is 0.43, 0.42, 0.4 and 0.4 min, respectively, which shows that the trypsin/zeolite ZSM-5 hemostatic composition has a procoagulant effect in both normal blood and coagulation factor X, VIII, IX, XI deficient blood, and the clotting time is greatly shortened. The trypsin/zeolite ZSM-5 hemostatic composition can promote coagulation for patients with hemophilia. As a control, when the zeolite ZSM-5 was added into all above-mentioned deficient blood, all the blood did not coagulate for a long time. From the comparison between Example 9 and Comparative Examples 18, it can be seen that the coagulation effect of the trypsin/zeolite ZSM-5 hemostatic composition is far better than that of the zeolite ZSM-5 or trypsin, and the coagulation time is greatly shortened.

Example 10

Preparation of Trypsin/Zeolite ZSM-5/Zeolite Y Hemostatic Composition:

(1) The zeolite ZSM-5 (Na type) with microporous channels and the atomic ratio of silicon to aluminum of 20 and zeolite Y (Na type) with microporous channels and the atomic ratio of silicon to aluminum of 4 are impregnated with a 5 M magnesium chloride solution at room temperature for 12 h to obtain the zeolite. The zeolite contains divalent magnesium ions and the number of divalent magnesium ions accounts for 95% of the total number of the metal cations outside the zeolite framework, and the number of monovalent sodium ions accounts for 5%.

(2) Disperse the 25 mg of zeolite ZSM-5 and zeolite Y (1:1) in the 1 mL aqueous solution to form a suspension of the zeolite ZSM-5 and zeolite Y; mix the suspension and trypsin at 25° C. for 30 min (the mass ratio of trypsin to zeolite ZSM-5 and zeolite Y; is 1:10) to make trypsin adsorb on the surface of zeolite; and dry the above solution in vacuum at −20° C. for 5 h to obtain the trypsin/zeolite ZSM-5/zeolite Y hemostatic composition.

The natural coagulation time of the trypsin/zeolite ZSM-5/zeolite Y hemostatic composition is 0.34 min, and the clotting time of coagulation factor X, VIII, IX, XI deficient blood is 0.33, 0.32, 0.4 and 0.34 min, respectively, which shows that the trypsin/zeolite ZSM-5/zeolite Y hemostatic composition has a procoagulant effect in both normal blood and coagulation factor X, VIII, IX, XI deficient blood, and the clotting time is greatly shortened. The trypsin/zeolite ZSM-5/zeolite Y hemostatic composition can promote coagulation for patients with hemophilia. The coagulation effect of the trypsin/zeolite ZSM-5/zeolite Y hemostatic composition is far better than that of the zeolite or trypsin, and the coagulation time is greatly shortened.

Example 11

Preparation of Trypsin/Mordenite/Zeolite X Hemostatic Composition:

(1) The mordenite (Na type) with microporous channels and the atomic ratio of silicon to aluminum of 20 and zeolite X (Na type) with microporous channels and the atomic ratio of silicon to aluminum of 1.2 are impregnated with a 5 M magnesium chloride solution at room temperature for 12 h to obtain the zeolite. The zeolite contains divalent magnesium ions and the number of divalent magnesium ions accounts for 95% of the total number of the metal cations outside the zeolite framework, and the number of monovalent sodium ions accounts for 5%.

(2) Disperse the 25 mg of mordenite and zeolite X (1:1) in the 1 mL aqueous solution to form a suspension of the mordenite and zeolite X; mix the suspension and trypsin at 25° C. for 30 min (the mass ratio of trypsin to mordenite and zeolite X; is 1:10) to make trypsin adsorb on the surface of zeolite; and dry the above solution in vacuum at −20° C. for 5 h to obtain the trypsin/mordenite/zeolite X hemostatic composition.

The natural coagulation time of the trypsin/mordenite/zeolite X hemostatic composition is 0.4 min, and the clotting time of coagulation factor X, VIII, IX, XI deficient blood is 0.43, 0.37, 0.4 and 0.36 min, respectively, which shows that the trypsin/mordenite/zeolite X hemostatic composition has a procoagulant effect in both normal blood and coagulation factor X, VIII, IX, XI deficient blood, and the clotting time is greatly shortened. The trypsin/mordenite/zeolite X hemostatic composition can promote coagulation for patients with hemophilia. The coagulation effect of the trypsin/mordenite/zeolite X hemostatic composition is far better than that of the zeolite or trypsin, and the coagulation time is greatly shortened.

Wherein, the mass ratio of the zeolite and deionized water in the zeolite suspension of Examples 1-11 of the present disclosure is 1:0.5 to 1:20; preferably, the mass ratio of the zeolite and deionized water in the zeolite suspension is 1:0.8 to 1:10; preferably, the mass ratio of the zeolite and deionized water in the zeolite suspension is 1:1 to 1:5; preferably, the mass ratio of the zeolite and deionized water in the zeolite suspension is 1:1.5 to 1:2.5.

In some embodiments, the suspension of the zeolite in Examples 1-11 of the present disclosure is subjected to ultrasonic treatment.

In some embodiments, the time of the ultrasonic treatment in Example 1-11 of the present disclosure is 0.5-30 min, the ultrasonic frequency is 20-200 kHz, and the ultrasonic power is 200-5000 W.

In some embodiments, the temperature of the mixing treatment of trypsin and zeolite in Example 1-11 of the present disclosure is 10 to 37° C.; preferably, the temperature of the mixing treatment is 15 to 30° C.; preferably, the temperature of the mixing treatment is 20 to 25° C.

In some embodiments, in the Example 1-11 of present disclosure, after the trypsin is adsorbed on the surface of the zeolite, it further includes freeze-drying the suspension of the zeolite and the trypsin. Preferably, the temperature of the freeze-drying process is 0° C. to −80° C.; preferably, the temperature of the freeze-drying process is −10° C. to −60° C.; preferably, the temperature of the freeze-drying process is −20° C. to −50° C.; preferably, the temperature of the freeze-drying process is −30° C. to −45° C.

In summary, in order to achieve the procoagulant effect of the hemostatic composition of the present invention, a specific mass ratio of zeolite to trypsin (1:200-4:10), a specific metal cation (divalent metal ion) outside the zeolite framework, and a specific zeolite pore size (micropores) must be required. The synergistic effect of all three elements is indispensable to form the hemostatic composition with excellent hemostatic properties of the present disclosure. Through the specific combination of inorganic materials and biological macromolecules, the procoagulant performance of the hemostatic composition of trypsin and zeolite is equal to or even better than that of thrombin alone, which can greatly reduce the cost of hemostatic materials and has more commercial prospects.

The present disclosure overcomes the prejudice of the prior art, and provides a bio-inorganic hemostatic composition that is fast to hemostasis, low in cost, and effective for hemophilia. The coagulation effect of the hemostatic composition is far better than that of zeolite or trypsin alone, the coagulation time is greatly shortened, and the blood loss is significantly reduced. The zeolite (microporous pore structure, divalent metal cation, specific mass ratio of zeolite to trypsin) in the hemostatic composition of the present disclosure positively regulates the spatial conformation and spatial orientation of trypsin, so that the spatial conformation of trypsin on the surface is conducive to contact with prothrombin in the clotting cascade, thereby promoting the conversion of prothrombin into thrombin and increasing the procoagulant activity. The overall effect of the hemostatic composition constituted by the synergistic effect of trypsin and zeolite is much better than that of trypsin alone or zeolite alone, and its procoagulant activity is much better than that of trypsin alone and zeolite, and is even better than that of thrombin alone. When encountering unexpected massive bleeding, the hemostatic composition can effectively stop bleeding, reduce the risk of death from aortic bleeding, reduce the damage of important organs, and also have a good effect of promoting blood clotting for patients with hemophilia.

The above embodiments are only used to illustrate the present disclosure and are not used to limit the scope of the present disclosure. In addition, it should be understood that after reading the teaching of the present disclosure, those skilled in the art can make various changes or modifications to the present disclosure, and these equivalent forms also fall within the scope defined by the appended claims of the present application.

What is claimed is:

1. A hemostatic composition, comprising zeolite and trypsin, wherein pores of the zeolite have a pore diameter of less than 2 nm; wherein the zeolite contains divalent metal cations, and the mass ratio of the trypsin to the zeolite is 1:200-4:10.

2. The hemostatic composition of claim 1, wherein the divalent metal cations are selected from the group consisting of cobalt ion, nickel ion, calcium ion, magnesium ion and strontium ion.

3. The hemostatic composition of claim 1, wherein the mass ratio of the trypsin to the zeolite is 1:100 to 3:10; preferably, the mass ratio of the trypsin to the zeolite is 1:60 to 2.5:10; the mass ratio of the trypsin to the zeolite is 1:50 to 2:10; the mass ratio of the trypsin to the zeolite is 1:40 to 1.5:10; the mass ratio of the trypsin to the zeolite is 1:20 to 1:10.

4. The hemostatic composition of claim 1, wherein the number of divalent metal cations accounts for 50% to 95% of the total number of the metal cations outside the zeolite framework; preferably, the number of divalent metal cations accounts for 60% to 90% of the total number of the metal cations outside the zeolite framework; preferably, the number of divalent metal cations accounts for 65% to 85% of the total number of the metal cations outside the zeolite framework; preferably, the number of divalent metal cations accounts for 70% to 80% of the total number of the metal cations outside the zeolite framework; preferably, the number of divalent metal cations accounts for 72% to 78% of the total number of the metal cations outside the zeolite framework.

5. The hemostatic composition of claim 1, wherein an atomic ratio of silicon to aluminum of the zeolite is 1-20.

6. The hemostatic composition of claim 1, wherein the zeolite is selected from the group consisting of zeolite A, chabazite, zeolite β, mordenite, zeolite X, zeolite Y, and zeolite ZSM-5.

7. A hemostatic composite material, wherein the hemostatic composite material comprises the hemostatic composition according to claim 1 and additives.

8. The hemostatic composite material of claim 7, wherein the additives are selected from the group consisting of carriers, antibacterial materials, antistatic materials, and polymer polysaccharides.

9. The hemostatic composite material of claim 8, wherein the carriers are selected from the group consisting of cotton, silk, wool, plastic, cellulose, rayon, polyester, polyurethane, polyethylene foam, polyacrylic acid foam, low-density polyether, polyvinyl alcohol, and polymethyl methacrylate.

10. The hemostatic composite material of claim 8, wherein the antibacterial materials are selected from the group consisting of silver nanoparticles, vanillin, and ethyl vanillin compounds.

11. The hemostatic composite material of claim 8, wherein the polymer polysaccharides are selected from the group consisting of cellulose, lignin, starch, chitosan, and agarose.

* * * * *